United States Patent [19]

Berg et al.

[11] Patent Number: 5,264,086
[45] Date of Patent: Nov. 23, 1993

[54] SEPARATION OF FORMIC ACID FROM ACETIC ACID BY AZEOTROPIC DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 11,242

[22] Filed: Jan. 29, 1993

[51] Int. Cl.$^5$ .............................. B01D 3/36
[52] U.S. Cl. ....................... 203/68; 203/67; 562/608; 562/609
[58] Field of Search ............. 203/67, 70, 68; 562/608, 609

[56] References Cited

U.S. PATENT DOCUMENTS

| | | | |
|---|---|---|---|
| 1,813,636 | 7/1931 | Petersen et al. | 203/67 |
| 3,024,170 | 3/1962 | Othmer et al. | 203/67 |
| 3,718,545 | 2/1973 | Horlenko | 203/70 |

FOREIGN PATENT DOCUMENTS 352879  10/1972  U.S.S.R. ................. 203/67

OTHER PUBLICATIONS

"Azeotropic Data—III", Horsley, published by American Chemical Society, Washington, D.C., 1973, p. 66.

Primary Examiner—Wilbur Bascomb, Jr.

[57] ABSTRACT

Formic acid difficult to separate from acetic acid by conventional distillation or rectification because of the close proximity of their boiling points. Formic acid can be readily separated from acetic acid by using azeotropic distillation. Effective agents are cyclopentane and tetrachloroethylene.

1 Claim, No Drawings

SEPARATION OF FORMIC ACID FROM ACETIC ACID BY AZEOTROPIC DISTILLATION

FIELD OF THE INVENTION

This invention relates to a method for separating formic acid from acetic acid using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Formic acid has been separated from acetic acid commercially using benzene as the azeotrope forming agent but because of the hazardous characteristics of benzene, its use has been largely abandoned. Carbon tetrachloride and cyclohexane have been reported but are not as effective as benzene as an azeotrope former.

Formic acid, B.P. 101° C. and acetic acid, B.P. 118° C. have a relative volatility of 1.23 and are difficult to separate by conventional rectification. Table 1 shows that to get 99% purity, sixty actual plates are required. For an agent giving a relative volatility of 1.34, 43 actual plates are required and with a relative volatility of 1.44, only 33 actual plates are required. An improvement of this magnitude represents a clear economic and operational advantage to the separation of these industrially important chemicals.

TABLE 1

Theoretical and Actual Plates Required vs. Relative Volatility for Formic Acid - Acetic Acid Separation

| Relative Volatility | Theoretical Plates Required At Total Reflux, 99% Purity | Actual Plates Required, 75% Eff. |
|---|---|---|
| 1.23 | 45 | 60 |
| 1.34 | 32 | 43 |
| 1.44 | 25 | 33 |

OBJECTIVE OF THE INVENTION

The object of this invention is to provide a process or method of azeotropic distillation that will enhance the relative volatility of formic acid to acetic acid in their separation in a rectification column. It is a further object of this invention to identify certain organic compounds that are stable, are effective as azeotropic distillation agents and can be readily separated from formic acid or acetic acid and recycled to the azeotropic distillation column with little decomposition.

SUMMARY OF THE INVENTION

The objects of this invention are provided by a process for the separation of formic acid from acetic acid which entails the use of certain organic compounds when separately employed as the agent in azeotropic distillation.

DETAILED DESCRIPTION OF THE INVENTION

We have discovered that certain organic compounds will effectively increase the relative volatility between formic acid and acetic acid during rectification when employed as the agent in azeotropic distillation. Table 2 summarizes the data obtained with these agents in a rectification column. The agents which are effective are cyclopentane and tetrachloroethylene.

TABLE 2

Data From Runs Made In Rectification Column

| Azeotrope Former | Temperature @ 640 mm. Overhead | Stillpot °C. | Azeo. Comp. Wt % Formic | Agent | Relative Volatility |
|---|---|---|---|---|---|
| Cyclopentane | 42 | 110 | 16 | 84 | 1.44 |
| Tetrachloroethylene | 84 | 105 | 50 | 50 | 1.34 |

2-Pentanone and 3-pentanone form azeotropes with formic acid but their relative volatilities are less than 1.23, the relative volatility of formic acid to acetic acid.

THE USEFULNESS OF THE INVENTION

The usefulness or utility of this invention can be demonstrated by referring to the data presented in Tables 1 and 2. Both of the successful agents show that formic acid can be separated from acetic acid by means of azeotropic distillation in a rectification column and that the ease of separation as measured by relative volatility is considerable.

WORKING EXAMPLES

Example 1

Fifty grams of formic acid, 50 grams of acetic acid and 50 grams of cyclopentane were charged to a glass perforated plate rectification column containing 7.3 theoretical plates. After five hours at total reflux, overhead and bottoms samples were taken and analyzed by gas chromatography. The overhead was 92% formic acid, 8% acetic acid; the bottoms was 45% formic acid, 55% acetic acid which is a relative volatility of 1.44.

Example 2

Fifty grams of formic acid, 50 grams of acetic acid and 50 grams of tetrachloroethylene were charged to the glass perforated plate rectification column. After five hours at total reflux, overhead and bottoms samples were taken and analysed. The overhead was 87% formic acid, 13% acetic acid, the bottoms was 45% formic acid, 55% acetic acid which is a relative volatility of 1.34.

We claim:

1. A method for recovering formic acid from a mixture of formic acid and acetic acid which comprises distilling a mixture of formic acid and acetic acid in the presence of an azeotrope forming agent, recovering the formic acid and the azeotrope forming agent as overhead product and obtaining the acetic acid from the stillpot, wherein said azeotrope forming agent is cyclopentane.

* * * * *